United States Patent [19]

Geusz et al.

[11] Patent Number: 5,151,353
[45] Date of Patent: Sep. 29, 1992

[54] PROCESS OF USING BACTERIA THAT METABOLIZE PHENYLACETATE THROUGH MANDELATE

[75] Inventors: Steven D. Geusz, Silver Spring; David M. Anderson, Rockville, both of Md.

[73] Assignee: ChemGen Corporation, Gaithersburg, Md.

[21] Appl. No.: 667,661

[22] Filed: Mar. 11, 1991

Related U.S. Application Data

[62] Division of Ser. No. 140,108, Dec. 31, 1987, Pat. No. 4,999,292.

[51] Int. Cl.$^5$ .......................... C12P 39/00; C12P 7/24; C12N 9/88; C12R 1/40
[52] U.S. Cl. ..................... 435/147; 435/42; 435/142; 435/146; 435/170; 435/232; 435/252.1; 435/252.34; 435/253.3; 435/877
[58] Field of Search ................ 435/42, 147, 142, 146, 435/170, 252.1, 252.34, 253.3, 253.6, 183, 232

[56] References Cited

PUBLICATIONS

Kennedy et al, Biochem. J. (1968) vol. 107, pp. 497–506.
"Enzyme Nomenclature" 1984 Academic Press 1984, pp. 394–395.

Primary Examiner—Herbert J. Lilling
Attorney, Agent, or Firm—Foley & Lardner

[57] ABSTRACT

Bacteria that metabolize phenylacetate along a mandelate-to-cis,cis-muconate pathway are disclosed. Bacteria that express the pathway for metabolizing phenylacetate through a mandelate intermediate can be isolated reproducibly by first selecting bacteria that can utilize both L-phenylalanine and mandelate as the sole carbon source and then blocking alternate pathways for the degradation of L-phenylalanine. The activity of selected enzymes along the mandelate-to-cis,cis-muconate pathway can be blocked in these bacteria to effect the accumulation of selected intermediates.

4 Claims, 1 Drawing Sheet

PROCESS OF USING BACTERIA THAT METABOLIZE PHENYLACETATE THROUGH MANDELATE

This application is a division, of application Ser. No. 07/140,108, filed Dec. 31, 1987, now U.S. Pat. No. 4,999,292.

BACKGROUND OF THE INVENTION

The present invention relates to bacteria that metabolize phenylacetate via a mandelate pathway. More particularly, the present invention relates to a new group of bacteria characterized by an ability to produce valuable compounds, including natural benzaldehyde, mandelate, benzyl alcohol, benzoate and cis,cis-muconic acid, which correspond to various intermediates along the aforesaid pathway.

A major use of benzaldehyde is as an ingredient in natural cherry flavors. An undesirable feature of the known processes for preparing benzaldehyde from products like apricot kernels or reground press cake, as disclosed in U.S. Pat. No 1,416,128, is that toxic hydrocyanic acid, along with benzaldehyde, is produced which must be separated completely from the benzaldehyde. U.S. Pat. Nos. 4,617,419, and 4,673,766, disclose the production of benzaldehyde from cinnamaldehyde according to a retro-aldol reaction, without production of toxic side products. But the disclosed process requires a source of cinnamaldehyde, which may have to be distilled or extracted prior to reaction.

A living organism that degrades a carbohydrate feedstock, or L-phenylalanine, along a catabolic pathway having a benzaldehyde intermediate could provide a source for the production of natural benzaldehyde. Earlier studies have suggested that pathways for the degradation of L-phenylalanine and phenylacetate along a mandelate pathway may occur in certain insects (Towers et al. (1972) *Can. J. Zool.* 50(7): 1047–1050), micro-algae (Landymore et al. (1978) *Phycologia* 17(3): 319–328), and fungi (Hockenhull et al. (1952) *Biochem. J.* 50: 605–609 and *Bioprocessing Technology* (1987) 9(11): 2–3).

However, it was generally understood heretofore that bacteria could not metabolize phenylacetate via a mandelate pathway, thereby to produce a desired intermediate like benzaldehyde. In this regard, the phrase "mandelate pathway" refers to that series of enzymatic degradations that converts mandelate to cis,cis-muconic acid. Intermediates of the degradation include benzoylformate, benzaldehyde, benzoate and catechol. In accordance with standard terminology, the names used to refer to acid intermediates reflect their actual form in vivo (i.e., in solution), thus mandelic acid is referred to as mandelate.

Such a pathway is known to exist in both *Pseudomonas* (e.g., Stevenson et al. (1964) *Biochem. J.* 96: 354–362) and *Acinetobacter calcoaceticus* NCIB 8250 (e.g., Cook et al. (1975) *J. Gen. Microbiol.* 91: 325–337), but it is only revealed when the bacteria are provided with feedstock in the form of mandelate or some other intermediate further along the pathway. Mandelate or benzoylformate are not readily available as natural products. These and other intermediates are also too expensive to be of use as feedstocks in a commercial process for subsequent intermediates.

One early study tested the ability of a wide range of aromatic compounds, both metabolizable and nonmetabolizable, to induce enzymes of the mandelate pathway. (Hegeman (1966) *J. Bacteriol.* 91(3): 1140–1154). Phenylacetate and phenylpyruvate, both possible degradation intermediates of L-phenylalanine, were among the many compounds tested and were shown to induce activities for mandelate dehydrogenase and benzoylformate decarboxylase. But the link which allowed conversion of phenylacetate to mandelate was completely unknown, and available biochemical evidence shows that L-phenylalanine and phenylacetate are not metabolized through catechol to ketoadipate (Wheelis and Stanier (1970) *Genetics* 66: 245–266).

Consequently, the conversion of phenylacetate to mandelate by bacterial action has been considered infeasible heretofore, even though expression of such a pathway in bacteria could, in principle, enable the accumulation of valuable chemical compounds as intermediates, for example, of microbially mediated L-phenylalanine degradation.

SUMMARY OF THE INVENTION

It is therefore an object of the present invention to provide means whereby phenylacetate can be converted via bacteria to a useful intermediate along the mandelate pathway.

It is a further object of the present invention to provide a bacteria culture having the capability of metabolizing a carbohydrate feedstock or L-phenylalanine through a mandelate intermediate to accumulate different mandelate-pathway intermediates.

It is yet another object of the invention to provide natural benzaldehyde from benzoylformate produced by a mutant bacterium with the ability to metabolize L-phenylalanine through a mandelate intermediate.

In accomplishing the foregoing objects, there has been provided, in accordance with one aspect of the present invention, a microbial culture consisting essentially of bacteria capable of metabolizing phenylacetate through a mandelate intermediate as shown in FIG. 1. In a preferred embodiment, the microbial culture contains at least some bacterial cells that lack active benzoylformate decarboxylase enzyme and, hence, accumulate the mandelate-pathway intermediate benzoylformate.

In accordance with another aspect of the invention, a process is provided for isolating a bacterium which expresses a pathway for metabolizing phenylacetate through a mandelate intermediate, comprising the steps of mutating bacteria that can metabolize phenylalanine and mandelate, and then selecting from the mutated bacteria cells in which the routes of L-phenylalanine degradation other than a phenylacetate-to-mandelate pathway are blocked. A preferred method of blocking the alternate pathways is by transposon mutagenesis. In one preferred embodiment, the samples to be cultured are collected from an ecological site that is exposed to a high concentration of L-phenylalanine.

In accordance with yet another aspect of the invention, a process is provided for the production of natural benzaldehyde in which bacterial benzoylformate decarboxylase is added to benzoylformate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
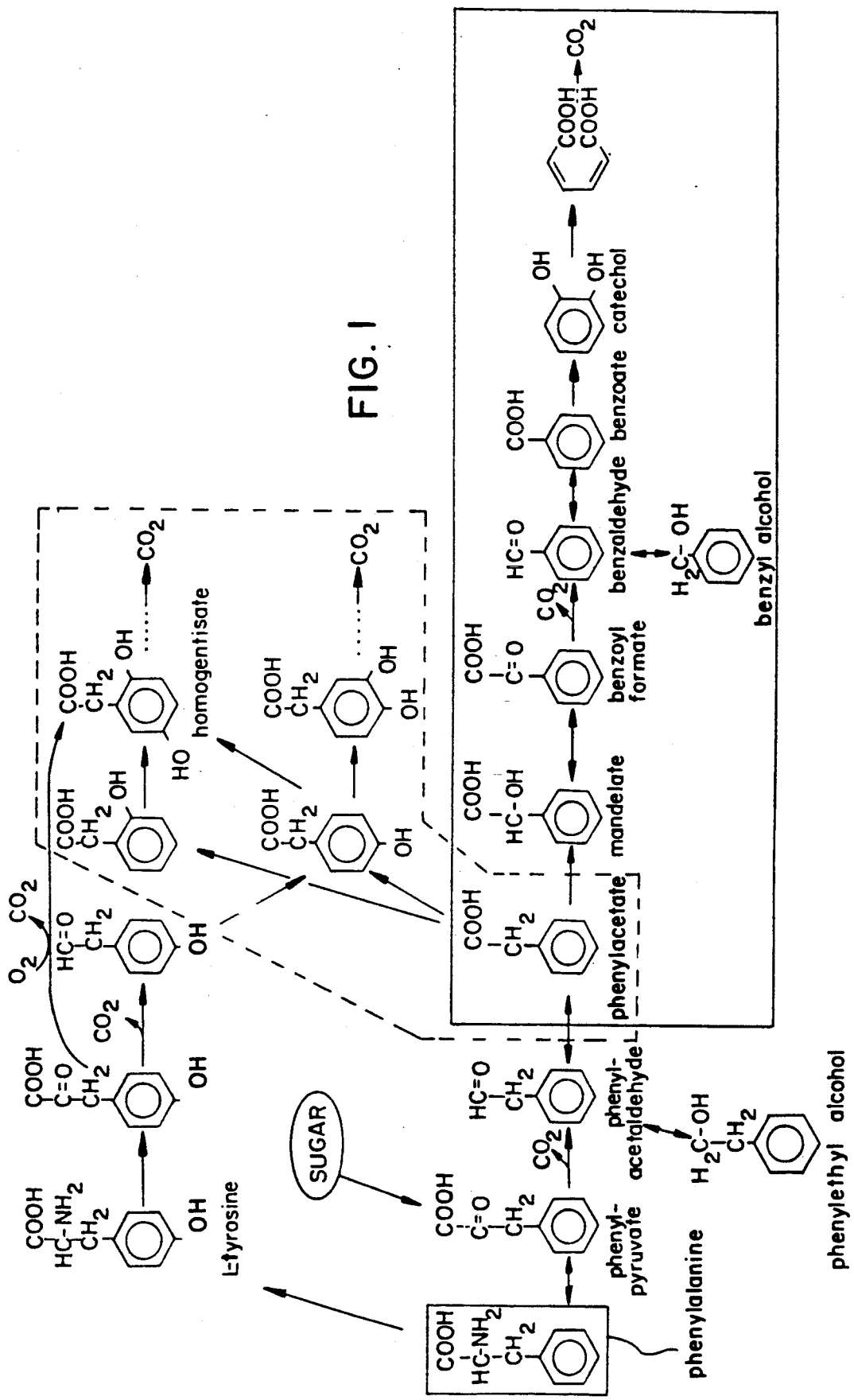
FIG. 1 is a composite diagram showing, inter alia, the aerobic catabolism of L-phenylalanine in bacteria.

It has been discovered that a number of commercially valuable compounds, including natural benzaldehyde, mandelate, benzyl alcohol, benzoate and cis,cis-muconic acid, can be produced via bacterial fermentation by exploiting a metabolic pathway previously thought not to be expressed in bacteria. This pathway, shown diagrammatically in the solid block in FIG. 1, has been found in a range of bacterial strains that can be obtained reproducibly, in accordance with the present invention, as a subset of the group of bacteria characterized by an ability to grow on both mandelate and L-phenylalanine, respectively, as the sole carbon source.

This ability is believed widespread among the bacteria, such as the aerobic Pseudomanads, which are well characterized in this regard. See Stanier et al. (1966) *J. Gen. Microbiol.* 43: 159-271. Pseudomonad strains that grow both on D,L-mandelate and L-phenylalanine include *P. aeurqenosa, P. putida, P. multivorans,* and *P. fluorescens.*

In accordance with the present invention, an initial selection for bacteria that can utilize both L-phenylalanine and mandelate as the sole carbon source, followed by mutagenesis to block alternative routes for the degradation of L-phenylalanine, results in bacteria which express a pathway for the conversion of phenylacetate to mandelate. In a preferred embodiment, the selection prior to mutagenesis is followed by a screening of the bacteria for an ability to grow on phenylacetate.

The bacteria of the present invention catabolize mandelate to cis,cis-muconate along the mandelate pathway, as described above. The exact mechanism by which the phenylacetate-to-mandelate pathway is expressed is not known, but such expression is obtained reproducibly when alternate routes of phenylacetate degradation are blocked.

In bacteria the established route of phenylacetate degradation is one of the ring-hydroxylation pathways, shown in the dotted block in FIG. 1. Bacteria that express a pathway for the conversion of phenylalanine to mandelate are obtained by blocking the ring-hydroxylation route(s) through mutagenesis. Certain bacteria can also metabolize phenylalanine to produce tyrosine. It is not necessary to block this latter pathway in order to get expression of the phenylalanine-to-mandelate conversion. Furthermore, the phenylalanine to tyrosine pathway has been identified in some strains as a slow-growth pathway that does not greatly diminish the production of mandelate intermediates from phenylalanine in accordance with the present invention. To optimize production of intermediates of the mandelate pathway, however, it is preferable that this alternative route also be blocked. Blocking the mandelate pathway at specific points is accomplished by further mutagenesis, allowing selected intermediates of commercial importance to be produced.

Mutagenesis can be carried out by any of several well-known techniques, such as by transposon insertion or by treatment with a known mutagenic agent like ethane methyl sulfonate, nitrosoguanidine or ultraviolet radiation. Alternatively, mutant alleles can be shifted among various mutant strains by use of a suitable transducing phage. See, e.g., Holloway et al. (1979) *Microbiological Reviews* 43: 73-102, and Ledoux (ed.), INFORMATIVE MOLECULES IN BIOLOGICAL SYSTEMS 223-33 (Holland Press 1971), the contents of which are hereby incorporated by reference.

After mutagenesis, in accordance with the present invention, characterization of the mutation can be effected by testing the strains for growth on intermediates of L-phenylalanine degradation. By way of example, if a strain of bacteria is tested for growth on the intermediates of the mandelate pathway and exhibits growth on benzoylformate, but not on mandelate, the strain is characterized as having a mutation affecting mandelate dehydrogenase activity. The desired mutation is one affecting the phenylacetic acid hydroxylase activity used by the cell. This mutation blocks the normal ring-hydroxylation route of phenylacetate degradation resulting in strains that cannot grow on phenylacetate. It is blockage of this normal route that results in expression by these strains of the pathway for degradation of phenylacetate through a mandelate intermediate.

One preferred mutation method in this regard is transposon insertion. Transposons are DNA segments that have the ability to move as a unit, in a more or less random fashion, from one genetic locus to another. See, e g., Lewin, GENES 589-608 (John Wiley & Sons 1983). Various transposons are commercially available, e.g., from the *E. coli* Genetic Stocks Center (Yale University School of Medicine, New Haven, Conn.) and from the American Type Culture Collection (ATCC) in Rockville, Md.

Donor cells carrying a plasmid are used to move transposons into target cells via conjugation. At a frequency of approximately $1 \times 10^{-8}$, a transposon copy becomes inserted, before loss of the plasmid can occur, into a chromosome of a recipient organism. The transposon carries a marker, e.g., for antibiotic resistance, so that insertion can be detected. It is also necessary to have a means of selecting against the donor cells. Insertion of a transposon within a gene can result in a complete loss of gene function. If inserted within a structural gene, a transposon may inactivate the specific enzyme activity encoded by the gene, resulting in mutants that are blocked in the degradative biochemical pathway(s) comprising that enzyme.

The advantage of transposon mutagenesis is that, while the frequency of mutation is high, the probability of double events is extremely small and every clone containing the marker which arises in a translocation experiment is one identified as having suffered a single mutational event. See, e.g., Kleckner et al. (1977) *J. Mol. Biol.* 116: 125-150.

After a strain is obtained which converts phenylacetate to mandelate, further manipulations can be used both to increase the endogenous production of L-phenylalanine and to enhance the degradation of L-phenylalanine.

In the former context, deregulation of the L-phenylalanine synthetic pathway results in a microorganism that overproduces L-phenylalanine. This allows the use of inexpensive, carbohydratebased feedstocks, such as molasses, hydrolyzed or liquified starch compositions, and high-fructose corn syrup, as a starting material for the manufacture of desirable compounds.

Bacterial strains which overproduce amino acids have commonly been produced by the use of analogs, e.g., halogenated amino acids, that mimic the regulatory effect of the natural compound. See Gollub et al. (1973) *J. Bacteriol.* 115: 121–128, and Im & Pittard (1971) *J. Bacteriol.* 106: 784–790, both incorporated herein by reference. These analogs cannot be used by the cell, but do act as corepressors or feedback inhibitors of enzymes responsible for amino acid biosynthesis. Thus, the cells are starved for required amino acids.

By selecting for cells able to grow in the presence of the analogs, strains with repressor mutations or feedback-resistant enzyme systems are obtained. The lack of negative regulation in these cells results in increased amino acid synthesis. By using multiple analogs, affecting different regulatory enzymes for the synthetic pathway, further increases in the production of the particular amino acid are possible. Bacteria according to the present invention which secrete greater amounts of L-phenylalanine have been selected by their resistance to both 3-fluorophenylalanine and 4-fluorophenylalanine.

Greater yields of L-phenylalanine can be achieved by combining analog resistance with auxotrophic mutations. See Fawcett et al. (1976) *Biochem. J.* 157: 651. In bacteria the three aromatic amino acids (tyrosine, L-phenylalanine and tryptophan) are usually formed from a common intermediate, chorismic acid. Blocking the synthetic routes to tyrosine and tryptophan by mutation can result in additional intercellular amounts of L-phenylalanine. In these auxotrophs, starvation for the required amino acids should cause constitutive induction of the chorismate pathway synthetic enzymes, leading to increased production of L-phenylalanine. This strategy has been utilized for the production of L-phenylalanine in *Corynebacterium* (Hagino and Nakayama (1974) *Agric. Biol. Chem.* 38: 157).

Genetic modifications can also be made to increase the L-phenylalanine degradative capability by elevating the rates of subsequent degradative steps, thus reducing the accumulation and possible secretion of L-phenylalanine. This draining of the L-phenylalanine synthetic pathway should also alleviate repression and feedback inhibition of synthetic enzymes, as discussed above, leading to increased yield.

The final step in the synthetic pathway from chorismic acid to L-phenylalanine utilizes a transaminase reaction to form L-phenylalanine from phenylpyruvate. The reverse reaction is the first stage of L-phenylalanine degradation in the desired pathway. In some strains another enzyme, L-amino acid dehydrogenase or phenylalanine deaminase, will also carry out this reaction. If the transaminase and dehydrogenase activity is removed by mutation, phenylpyruvate formed from chorismic acid may be used in production of mandelate pathway intermediates. Bypassing the synthesis of L-phenylalanine in this way allows external regulation of L-phenylalanine availability. By causing L-phenylalanine starvation at the desired time, increased formation of phenylpyruvate is induced. The phenylpyruvate is metabolized via mandelate, resulting in increased product formation. Starvation for L-phenylalanine also releases any remaining repression, feedback inhibition, and attenuation that moderates the carbon flow in the L-phenylalanine pathway.

The second enzyme of the desired pathway, phenylpyruvate decarboxylase, can also be manipulated to improve L-phenylalanine degradation. This enzyme has been identified as the rate-limiting step in the flow of carbon from L-phenylalanine to L-mandelate. Because the decarboxylation is essentially irreversible, increasing this enzyme activity will greatly shift the equilibrium of earlier reactions towards completion. Mutants with a more proficient phenylpyruvate decarboxylase can be identified by their larger colony size on L-phenylalanine agar after treatment with mutagens. Alternatively, continuous dilution of cultures growing on L-phenylalanine broth can be used to select for the more rapidly growing mutants. It has been discovered that some phenylalanine analog resistant mutants have increased phenylpyruvate decarboxylase enzyme activity.

Pursuant to the present invention, L-phenylalanine or carbohydrate-based feedstocks can be used as the feedstock in a fermentation process in order to produce the desired product in high purity economically and naturally. In this context, "fermentation" is used broadly to refer to any controlled microbial action by which useful products are obtained from the substrate(s) of that action. In accordance with the present invention, fermentation can be carried out in a stirred-tank reactor, a closed cylindrical tank containing agitators, baffles, heat exchange coils, and automatic controls for temperature, air flow, pressure, pH, and foaming. A fermenter of this sort would be charged with essential nutrients and the feedstock, sterilized and inoculated with a rapidly growing culture consisting essentially of bacteria mutationally blocked for the enzymatic degradation of the desired intermediate. Other microbial cells may be present, so long as they do not interfere with the production of the desired intermediate by bacteria within the present invention.

Continuous culture can increase fermenter productivity by eliminating the downtime of batch cultures. However, it is difficult to maintain sterility in large scale continuous cultures. Accordingly, batch fermentations which utilize the bacteria of the present invention are preferred.

Commercially valuable compounds along the mandelate pathway include cis,cis-muconic acid, which is useful as a plastic monomer (see U.S. Pat. Nos. 4,588,688, 4,555,107 and 4,535,059), as well as benzaldehyde and benzyl alcohol, both useful flavoring constituents. Another pathway intermediate, benzoate, is useful as a natural preservative. Mandelate, which is useful as a drug precursor (see U.S. Pat. Nos. 3,957,758 and 4,391,826), is also an intermediate in the pathway. In order to accumulate a particular intermediate, mutagenesis is employed, as described above, to block activity of the enzyme that converts the intermediate of interest to the next intermediate on the pathway. For example, a block of muconate lactonizing enzyme results in an accumulation of cis,cis-muconate.

In some cases, it may be desirable to stop the pathway at a step earlier than the desired intermediate, e.g., if the intermediate accumulated is toxic to the bacteria, as is the case with benzaldehyde. In a process for producing natural benzaldehyde, it is desirable to accumulate benzoylformate rather than benzaldehyde because aldehydes are generally very reactive toward sulfhydryl and amino groups in enzymes (protein) and tend rapidly to inactivate their activity. Benzaldehyde, in particular, is an effective biocide at concentrations much lower than would be necessary for economical production. By stopping the pathway at benzoylformate, pursuant to the present invention, and then converting the benzoylformate in an enzymatic reactor with benzoylformate decarboxylase, toxic effects on the bacteria can be avoided.

Surprisingly, benzoylformate decarboxylase enzyme obtained from bacteria that can metabolize mandelate to benzoic acid (see FIG. 1) has been found to remain active and operate at favorable rates even in the presence of saturating concentrations of benzaldehyde (the solubility of benzaldehyde in water is 0.33 g per 100 ml). Although any bacterium having the mandelate-to-benzoic pathway can be used in this regard, bacteria that have been selected for their ability to grow on both mandelate and phenylalanine, as described previously, are preferred as a source for the benzaldehyde-resistant benzoylformate decarboxylase (hereafter "bacterial benzoylformate decarboxylase"). Alternatively, conventional recombinant-DNA techniques can be applied to isolate and clone from suitable bacteria the gene coding for the aldehyde-resistant decarboxylase, and that gene can be used to transform *E. coli* or some other microbial strain from which the enzyme is then derived. Established genetic manipulations, such as an increase in gene copy number or promoter fusions, could also be employed to effect an overproduction of bacterial benzoylformate decarboxylase.

Even in emulsions in which the concentration of benzaldehyde is 5%, bacterial benzoylformate decarboxylase retains significant activity. This is highly unexpected since aldehydes are generally very reactive toward sulfhydryl and amino groups of proteins, and hence tend rapidly to inactivate enzymes. Accordingly, bacterial benzoylformate decarboxylase can be employed, pursuant to the present invention, in converting benzoylformate into benzaldehyde. For example, the double mutant of a strain expressing the desired pathway in which the activity of benzoylformate decarboxylase has been blocked will accumulate benzoylformate when grown on L-phenylalanine. The accumulated benzoylformate can be converted to benzaldehyde by the action of bacterial benzoylformate decarboxylase activity in an enzymatic reactor.

As indicated below, bacterial benzoylformate decarboxylase was partially purified from soil isolates according to Hegeman, METHODS IN ENZYMOLOGY 88: 674, the contents of which are hereby incorporated by reference. So long as the activity of the enzyme is not significantly affected, however, the procedure by which the bacterial benzoylformate decarboxylase is obtained is not critical. For large-scale production, for example, several other preparatory methods could be used. For example, whole cells could be used, optionally with a 55° C. heat treatment to inactivate benzaldehyde dehydrogenase. Alternatively, the cells could first by lysed (in a continuous-flow homogenizer, for example), followed by a heat treatment of the lysate at 55° C. for ten minutes and filtration to remove particulate and coagulated denatured protein. Filtration could be through a celite-precoated rotary drum vacuum filter or an ultrafiltration device with a 150,000 molecular weight cutoff.

Bacterial benzoylformate decarboxylase was obtained, pursuant to Hegeman supra, using bacterial cells grown on mandelate or benzoylformate, which cells had been isolated from phenylalanine-rich soil via selection for growth on L-phenylalanine and mandelate, respectively (see Example 1 below). The bacterial benzoylformate decarboxylase produced by these cells, which were typed as *P. putida,* was used in a bioreactor to convert benzoylformate to benzaldehyde. Biochemical assays have also shown that a bacterial mutant lacking the ability to use phenylacetate (see Example 4 below) has a greatly enhanced activity of this enzyme. Such a mutant could therefore also serve as a source of increased amounts of bacterial benzoylformate decarboxylase.

The present invention is further described below by reference to the following illustrative examples.

EXAMPLE 1

Isolating Starting Material from the Soil

Specimens were collected from a site where spillage from the large-scale production of L-phenylalanine had contaminated the surrounding soil. Twenty grams of these soil samples were inoculated into four hundred milliliters of minimal culture media which contained a sodium/potassium phosphate buffer, an inorganic nitrogen source, and essential mineral salts. Carbon was supplied as 0.1% (w/v) glucose and 0.2% L-phenylalanine. Nystatin was added to 50 micrograms/ml to control fungal growth. Cultures were incubated at 34° C. with strong aeration by shaking at 400 rpm in 2 liter baffled flasks. After 24 hours, the culture broths were passed through a coarse milk filter to remove debris and divided 1:2 into fresh medium. Following an additional 24 hour incubation, cultures were filtered through Whatman No. 4 paper to clear fine particles and diluted 1:5 into minimal medium with 0.1% L-phenylalanine, 0.1% mandelic acid, and 0.05% glucose.

At daily intervals cultures were split 1:5 into fresh medium alternating between L-phenylalanine and mandelate as growth substrate. This schedule was utilized to enrich the cultures for organisms able to efficiently degrade both compounds, at rates required for an industrial process.

From day #7 until the end of the enrichment at day #17, samples from the cultures were diluted and plated on a rich agar medium to isolate candidate organisms. Individual colonies were then tested for growth on agar medium containing L-phenylalanine or mandelate to determine the effectiveness of the enrichment procedure. Microorganisms which grew on both substrates were preserved for further screening.

Isolates which exhibited growth on L-phenylalanine and mandelate were next assayed for the ability to utilize other proposed intermediates of L-phenylalanine degradation, including phenylacetate. Of the original 42 candidates isolated, 6 showed sufficient growth on substrates of the desired pathway, and little or no growth initially on compounds which would indicate an alternative degradative route (i.e., little or no growth on ring-hydroxylated intermediates). However, when grown on phenylacetate, the ability to grow on ring-hydroxylated intermediates was induced. Thus, selection for individual isolates which do not grow on the ring-hydroxylated intermediates is ineffective in selecting a strain which will directly express the phenylacetate-to-mandelate conversion.

EXAMPLE 2

Mutating the Starting Material to Block the Alternate Route of Phenylacetate Degradation The six selected strains, all gram-negative rods, were next examined for the ability to apply transposon mutagenesis methods in order to develop a production strain which was blocked for the passage of phenylacetate to the ring-hydroxylation pathway.

*E. coli* strain NC967 carries a narrow-hostrange plasmid which can be used to move a transposon (Tn10) into related bacteria via conjugation. See, e.g., Figurski et al (1979) *Proc. Nat'l. Acad. Sci. USA* 76: 1648-1652, the contents of which are hereby incorporated by reference. The vehicle for transposon transfer is plasmid pRK2013::Tn10.

Cells from the *E. coli* donor strain were mated with each of the selected strains by plating a 1:1 mixture of cells on solid media. After 12-18 hours incubation to allow plasmid transfer to occur, the cells were washed and replated on minimal glucose agar containing tetracycline to select for transconjugates. The *E. coli* donor cells are unable to grow on these plates due to a requirement for amino acid supplements. Thus, only recipient cells that have incorporated a transposon into their chromosome (becoming tetracycline resistant) will form colonies.

Of the six strains selected on the basis of growth on the desired substrates, two were found to mate with *E. coli* NC967 and accept the transposon efficiently. One of these two strains was subsequently identified as *P. putida* by the American Type Culture Collection (ATCC), Rockville, Md. This strain has been deposited with the ATCC and has been designated as ATCC No. 55012. The identification by the ATCC showed the following:

|  | *P. putida* | ATCC No. 55012 |
| --- | --- | --- |
| Motility | + | + |
| Polar multitrichous flagella | + | + |
| Aerobic metabolism | + | + |
| Fluorescent pigment | V* | + |
| Denitrification | − | − |
| Gelatin hydrolysis | − | − |
| Growth at 42° C. | − | − |
| Moellers medium |  |  |
| lysine | − | − |
| arginine | + | + |
| ornithine | − | − |
| Utilization as sole carbon source |  |  |
| D-glucose | + | + |
| benzylamide | + | + |
| glycine | + | + |
| trehalose | − | − |
| i-inositol | − | − |
| geraniol | − | − |

*V = variable (11-89% of *P. putida* strains test positive for this characteristic.

EXAMPLE 3

Identifying Mutants and Selecting Mutants Blocked the Alternative Route of Phenylacetate Degradation Colonies which had accepted the transposon were transferred to agar containing pathway intermediates to identify enzyme deficient mutants. By means of this mutation protocol, several mutant derivatives of one of the isolates, were identified and characterized.

The desired mutant was produced with Tn10. This mutant lacked only the ability to utilize phenylacetate as a carbon source and was subjected to an analysis of its L-phenylalanine degradation. Cell-free culture medium from high-density cultures growing on L-phenylalanine was acidified and extracted twice with ethyl ether. The ether was evaporated and the dried extracts were resuspended in aqueous 20% ethanol and separated by HPLC using a Bio-Rad HPX-87H HPLC column at 65° C. The mobile phase was 0.01N $H_2SO_4$, 10% acetonitrile, at a flow rate of 0.6 ml/min. Eluted compounds were detected by monitoring the absorbance at 205 nm.

Analysis of aromatic chemicals in culture broths revealed phenylacetate was the major product accumulated when cells were grown on L-phenylalanine. In similar studies with broth containing phenylacetate, the phenylacetate was not degraded. Previous experiments with the wild-type cells had shown that a hydroxylation of phenylacetate to form the 2-hydroxy derivative was the next degradative step. This indicated that the phenylacetate 2-hydroxylase enzyme activity had been inactivated by insertion of Tn10.

Other mutants were produced by transposon insertion. Mutations can be transferred from these mutants, via a transducing phage according to conventional methodology, into strains expressing the desired mandelate pathway in order to produce strains which concentrate desired intermediates.

For example, one such mutant was identified by its slow growth on agar containing D/L-mandelate, benzoylformate, or 1-phenyl-1,2-hydroxyethane (diol) as the sole carbon source. Growth rates comparable to those of the wild type isolate are seen when this mutant is grown on benzaldehyde or benzoic acid.

To identify the nature of the metabolic defect in this mutant standard methods were used for the assay of benzoylformate decarboxylase. See, e.g., Gunsalus et al. (1953) *J. Bacteriol,* 66: 548, the contents of which are hereby incorporated by reference. This enzyme converts benzoylformate to benzaldehyde and $CO_2$. Crude cell extracts from the mutant were found to have a decreased benzoylformate decarboxylase specific activity relative to cell extracts from the wild type. This indicated that partial loss of benzoylformate decarboxylase function had resulted from the insertion of Tn10. Accordingly, transfer of this mutation would result in partial loss of benzoylformate decarboxylase function in the recipient strain.

EXAMPLE 4

Expression of the Mandelate Pathway in Bacteria Blocked for the Alternative Route of Phenylacetate Degradation The mutant which lacked the ability to utilize phenylacetate was grown on media containing phenylacetate and produced at a low frequency some cells which spontaneously regained the ability to degrade phenylacetate. These cells remained tetracycline resistant, suggesting that there was not excision and loss of Tn10. When culture broth from one such spontaneously-growing mutant was subjected to analysis, via high pressure liquid chromatography (HPLC) after growth on phenylacetate, different intermediates accumulated than with wild-type cells grown under the same conditions. Mandelate and benzoate were identified as metabolic intermediates of these mutants based on UV spectra and HPLC retention times.

In the wild-type cells the conversion of phenylacetate to mandelate apparently proceeds at insignificant rates. Only by blocking the normal route of phenylacetate degradation are strains readily identified that are characterized by the ability to rapidly metabolize phenylacetate through a mandelate pathway.

EXAMPLE 5

Mutating with a Second transposon to Produce Double Mutants

After a strain which degrades phenylacetate by the mandelate pathway has been isolated, additional metabolic blocks may be introduced by the selective inactivation of degradative enzymes. The additional metabolic blocks allow degradation along the mandelate pathway to be "stopped" at various points, resulting in accumulation of the intermediate just prior to the enzymatic step blocked.

By way of example, double mutants of the mutant which lacked the ability to utilize phenylacetate have been obtained by the use of another transposon delivery system as described in Simon et al (1983) *Bio/Technology* 7(3): 784–791, the contents of which are hereby incorporated by reference. Although these double mutants were produced from the mutant which lacked the ability to utilize phenylacetate (a strain which did not express the desired phenylacetate-to-mandelate pathway) the same technique could be used to produce double mutants of a mutant strain that does express the phenylacetate-to-mandelate pathway. Thus, strains can be developed which are blocked at any desired intermediate.

Matings with the second *E. coli* donor strain, SM10(pSup2021), have been performed to convey Tn5 into single mutant strains. Transposon insertion was selected on the basis of resistance to kanamycin. Identification of double mutant strains was performed using techniques similar to those described above for identification of single mutants.

One of the mutant strains accumulated catechol when grown on benzoic acid. Thus, it was characterized as having a partial block of catechol 1,2-dioxygenase activity. Another mutant strain completely lost activity of an as yet unidentified enzyme resulting in a total loss of growth on the compounds of the mandelate pathway. The strain did not grow on the mandelate pathway intermediates, D/L-mandelate, benzoylformate, benzaldehyde, and benzoate, or the similar compounds, 4-hydroxy benzoate, and protocatechuate. Unlike the mutants that express the phenylalanine-to-mandelate conversion which spontaneously arise from mutants lacking the ability to utilize phenylacetate, this double mutant strain never yielded progeny with the ability to grow on phenylacetate. This provided further confirmation that the strain of Example 4 grew as a result of activation of the phenylacetate-to-mandelate enzymatic conversion.

As previously noted, an alternative method of producing double mutants from a mutant expressing the phenylacetate-to-mandelate conversion would be to move mutant alleles previously created in strains which do not express the desired pathway into a strain expressing the desired pathway by transduction with a suitable transducing phage. For example, the transduction of the deficient allele from the above-identified mutant in which benzoylformate decarboxylase (see Example 3) is blocked into a strain expressing the desired pathway would result in a strain that accumulates benzoylformate when grown on L-phenylalanine. Benzoylformate is an important precursor for the production of natural benzaldehyde.

EXAMPLE 6

Isolation of Benzoylformate Decarboxylase-Deficient Mutants

An overnight culture of the bacteria of Example 4 grown in YPD broth was centrifuged, washed, and resuspended in 5 ml saline. Final cell density had an absorbance at 600 nm of 0.7, corresponding to $4 \times 10^7$ cells/ml. Cells were irradiated on a platform agitator approximately 30 cm from a germicidal UV lamp. Exposure for 20 seconds was found to reproducibly kill 99.5% of the cells, near the optimum ratio for mutagenesis.

Indicator plates containing were used for the detection of mutants. This procedure provides a convenient and sensitive screening method for isolating blocked mutants. Diluting the irradiated cells 1:50 with saline and spreading 80 μl of this suspension yielded 600–700 surviving colonies on each 150 mm petri dish. Growth on tetrazolium plates (Bochner and Savageau (1977) *Appl. Environ. Microbiol.* 33(2):434–444) supplemented with 1 g/L D-mandelic acid was used to identify cells defective in enzymes of the mandelate pathway. In addition to substrate, these plates contained 7 g/L $K_2HPO_4$, 3 g/L $KH_2PO_4$, 0.1 g/L $MgSO_4$, 2 g/L proteose peptone, 25 mg/L 2,3,5-triphenyl tetrazolium chloride and 15 g/L agar. Several mutant colonies were identified by their lack of tetrazolium dye reduction, and were subjected to further screening.

Two mutant strains grew well on benzaldehyde and benzoic acid, but were unable to grow on mandelic acid or benzoylformate. This phenotype indicated a deficiency of the enzyme benzoylformate decarboxylase. Assays of benzoylformate decarboxylase activity in cell-free extracts showed that these strains displayed reduced activity for this enzyme, relative to the parent strain.

Benzoylformic acid was identified as a product of phenylacetate metabolism in one of the two strains through HPLC and spectrophotometric methods. Additional mutations and refined biotransformation conditions can improve the titer realized from use of this type of strain, and allow the efficient conversion from L-phenylalanine or a carbohydrate starting material.

EXAMPLE 7

Isolation of L-Phenylalanine Analog Resistant Mutants

Cells from an overnight culture of the bacteria of Example 4 were grown in 2 ml YPD broth, collected by centrifugation and diluted to $3 \times 10^7$ cells/mL ($A_{600}=0.5$). One hundred microliters of this suspension was plated onto a 100 mm petri dish of minimal media containing 1 g/L glucose and allowed to absorb into the agar. Approximately 5 mg of 4-fluoro L-phenylalanine, or 3-fluoro L-phenylalanine was placed in the center of the plate prior to incubation at 34° C. A cleared zone of growth inhibition appeared around the analog after 48 hours. Resistant colonies were detected in this cleared zone. Cells obtained from this region of the plates were preserved and later tested for the overproduction of L-phenylalanine.

As an alternative method, the L-phenylalanine analogs were added at a concentration of 10 mg/ml into minimal glucose media after the agar had been autoclaved and partially cooled. Fifteen milliliters of this media were added to 100 mm plates. An edge of these plates was elevated during hardening, causing the agar to harden at an angle. An equal volume of minimal media containing no analog was subsequently poured over the previous agar in each plate, and the dishes were placed on a level surface to cool. This procedure created a gradient of analog concentration on which cells were plated as described above. In this case, mutant colonies were obtained from a cleared zone corresponding to the higher analog concentrations.

Mutants isolated in these experiments were tested to determine if their analog resistance was manifested in an increased production of L-phenylalanine. Cells were grown in minimal glucose broth media to late log phase and then removed by centrifugation. Cell-free culture broth was assayed for the presence of free amino acids using ninhydrin reagent, following the procedure of Moore (1968) *J. Biol. Chem.* 243: 6281. Samples of the parent strain of Example 4 were prepared in an identical manner for comparison.

Several of the isolates were found to secrete higher amounts of ninhydrin-reacting material relative to the parent strain which is not resistant to fluorinated L-phenylalanine.

EXAMPLE 8

Preparation of Benzaldehyde from Benzoylformate using Bacterial Benzoylformate Decarboxylase Bacterial benzoylformate decarboxylase was used to produce benzaldehyde from commercially available benzoylformate in a bioreactor. The total reaction volume was 24 ml and comprised the following:
2.0 ml 0.1M benzoylformate
0.8 ml 0.5 mg/ml thiamine pyrophosphate
16.0 ml sodium phosphate buffer (0.1M, pH=6.0)
0.8 ml bacterial benzoylformate decarboxylase
4.4 ml $H_2O$ The bacterial benzoylformate decarboxylase was obtained from soil isolates and was partially purified through Step 5 according to Hegeman, supra. The temperature was kept at 25° C. and the pH was maintained at the pH of 6.0 by addition of sodium hydroxide. Nitrogen gas above the surface of the liquid prevented oxidation of reaction products. The mixture was reacted with continuous stirring. After 24 hours the reaction mixture was extracted. The production of benzaldehyde was confirmed by HPLC analysis.

As will be evident to those skilled in the art, various modifications of the present invention can be made without departing from its spirit or scope. As previously mentioned, for example, proper selection of bacteria produced in accordance with the present invention can allow a carbohydrate-based composition to replace L-phenylalanine as the feedstock in the fermentation process. Moreover, as the commercial importance of other intermediates along the mandelate pathway becomes apparent, suitable mutants blocked for production of the corresponding enzyme can be routinely produced pursuant to the present invention, to accumulate these intermediates. In this regard, certain of the mutant strains mentioned in the foregoing examples should be seen as merely illustrative of strains that can be employed, as indicated above, to make commercial use of the mandelate pathway. In accordance with the present invention, other strains can be produced that have a desired phenotype and that are at least equally as useful in exploiting the mandelate pathway.

What is claimed is:

1. A process for the production of natural benzaldehyde comprising the steps of:
   obtaining benzoylformate by a fermentation employing bacteria that can metabolize phenylacetate through a mandelate intermediate and that cannot metabolize benzoylformate,
   converting the benzoylformate into benzaldehyde via action of bacterial benzoylformate decarboxylase to effect an accumulation of benzaldehyde, and recovering said benzaldehyde.

2. A process according to claim 1 wherein said bacterial benzoylformate decarboxylase is obtained from Pseudomonas.

3. A process as recited in claim 1, wherein the bacterial benzoylformate decarboxylase is isolated from bacteria selected from their ability to grow on both mandelate and phenylalanine.

4. A process as recited in claim 3, wherein the benzoylformate is converted into benzaldehyde via action of said bacterial benzoylformate decarboxylase in an enzymatic reactor.

* * * * *